(12) United States Patent
McConnell et al.

(10) Patent No.: US 11,957,148 B2
(45) Date of Patent: *Apr. 16, 2024

(54) MIXTURE OF HUMAN MILK OLIGOSACCHARIDES(HMOS)

(71) Applicant: SOCIÉTÉ DES PRODUITS NESTLÉ S.A., Vevey (CH)

(72) Inventors: Bruce McConnell, La Tour de Peilz (CH); Louise Kristine Vigsnaes, København NV (DK)

(73) Assignee: Societe des Produits Nestle S.A., Vevey (CH)

( * ) Notice: Subject to any disclaimer, the term of this patent is extended or adjusted under 35 U.S.C. 154(b) by 1347 days.

This patent is subject to a terminal disclaimer.

(21) Appl. No.: 16/061,424

(22) PCT Filed: Dec. 15, 2016

(86) PCT No.: PCT/EP2016/081308
§ 371 (c)(1),
(2) Date: Jun. 12, 2018

(87) PCT Pub. No.: WO2017/103019
PCT Pub. Date: Jun. 22, 2017

(65) Prior Publication Data
US 2020/0260771 A1   Aug. 20, 2020

(30) Foreign Application Priority Data

Dec. 15, 2015  (EP) .................................... 15200067
Feb. 3, 2016   (EP) .................................... 16154144

(51) Int. Cl.
| | |
|---|---|
| *A61P 31/04* | (2006.01) |
| *A23L 33/00* | (2016.01) |
| *A23L 33/12* | (2016.01) |
| *A23L 33/135* | (2016.01) |
| *A23L 33/19* | (2016.01) |
| *A23L 33/195* | (2016.01) |
| *A61K 31/702* | (2006.01) |
| *A61P 31/12* | (2006.01) |

(52) U.S. Cl.
CPC ............ *A23L 33/40* (2016.08); *A23L 33/135* (2016.08); *A61K 31/702* (2013.01); *A61P 31/04* (2018.01); *A61P 31/12* (2018.01); *A23L 33/12* (2016.08); *A23L 33/19* (2016.08); *A23L 33/195* (2016.08); *Y02A 50/30* (2018.01)

(58) Field of Classification Search
None
See application file for complete search history.

(56) References Cited

U.S. PATENT DOCUMENTS

| | | | |
|---|---|---|---|
| 2011/0150851 A1 | 6/2011 | Schmitt et al. | |
| 2012/0172307 A1 | 7/2012 | Davis et al. | |
| 2012/0172311 A1 | 7/2012 | Nash et al. | |
| 2012/0172327 A1 | 7/2012 | Buck et al. | |
| 2012/0172330 A1 | 7/2012 | Buck et al. | |
| 2012/0172331 A1 | 7/2012 | Buck et al. | |
| 2014/0271562 A1 | 9/2014 | Garcia-Rodenas et al. | |

FOREIGN PATENT DOCUMENTS

| | | | | |
|---|---|---|---|---|
| EA | 201201281 A1 | 10/2013 | | |
| EP | 2454948 | 5/2012 | | |
| EP | 2465509 A1 | 6/2012 | | |
| EP | 2768314 A1 | 8/2014 | | |
| WO | 9843494 A1 | 10/1998 | | |
| WO | 2006022543 A1 | 3/2006 | | |
| WO | 2009059996 A1 | 5/2009 | | |
| WO | 2009082216 A1 | 7/2009 | | |
| WO | 2012076323 A1 | 6/2012 | | |
| WO | WO-2012076323 A1 * | 6/2012 | ............. | A23L 1/296 |
| WO | 2013032674 A1 | 3/2013 | | |
| WO | 2013154725 A1 | 10/2013 | | |
| WO | 2013185780 A1 | 12/2013 | | |
| WO | 2014070016 A1 | 5/2014 | | |
| WO | 2015071403 | 5/2014 | | |
| WO | 2014090261 A1 | 6/2014 | | |
| WO | 2014100191 A1 | 6/2014 | | |
| WO | WO-2014187464 A1 * | 11/2014 | ............. | A23L 33/10 |
| WO | 2015071389 A1 | 5/2015 | | |
| WO | 2015071391 A1 | 5/2015 | | |
| WO | 2015071401 | 5/2015 | | |
| WO | 2015071402 A1 | 5/2015 | | |
| WO | 2015100091 A1 | 7/2015 | | |
| WO | WO-2016014473 A1 * | 1/2016 | ............. | A23C 9/152 |
| WO | 2017103019 A1 | 6/2017 | | |
| WO | 2018206434 A1 | 11/2018 | | |

OTHER PUBLICATIONS

Lactodifucotetraose (Synonyms: Difucosyllactose ; 2',3-Difucosyllactose) retrieved on Nov. 28, 22 from https://www.medchemexpress.com/lactodifucotetraose.html.*

Feller, "Sugars in Breast Milk Protect Babies from Infection", Retrieved from https://www.upi.com/Health_News/2016/08/26/Sugars-in-breast-milk-protect-babies-from-infection/5111472228890, Aug. 26, 2016, 2 Pages.

Bode, "Human Milk Oligosaccharides: Every Baby Needs a Sugar Mama", Glycobiology, vol. 22, Issue No. 9, Apr. 8, 2012, pp. 1147-1162.

Parschat et al., "Fermentativ Erzeugte Humane Milch-Oligosaccharide Wirken Prabiotisch", Retrieved from https://prozesstechnik.industrie.de/food/wirken-praebiotisch/, Oct. 19, 2016, 3 Pages.

Notice of Opposition Received for EP Application No. 16809851.5, dated Jul. 8, 2020.

(Continued)

*Primary Examiner* — Oluwatosin A Ogunbiyi
(74) *Attorney, Agent, or Firm* — K&L Gates LLP

(57) ABSTRACT

The invention relates to a mixture of human milk oligosaccharides and composition comprising thereof, that consists essentially of: LNnT, LNT, 2'-FL, 3'-SL, 6'-SL and either DFL or 3-FL, preferably DFL, that can be useful for preventing and/or treating viral and/or bacterial infections in a human.

7 Claims, 2 Drawing Sheets

(56) References Cited

OTHER PUBLICATIONS

Figure 1:
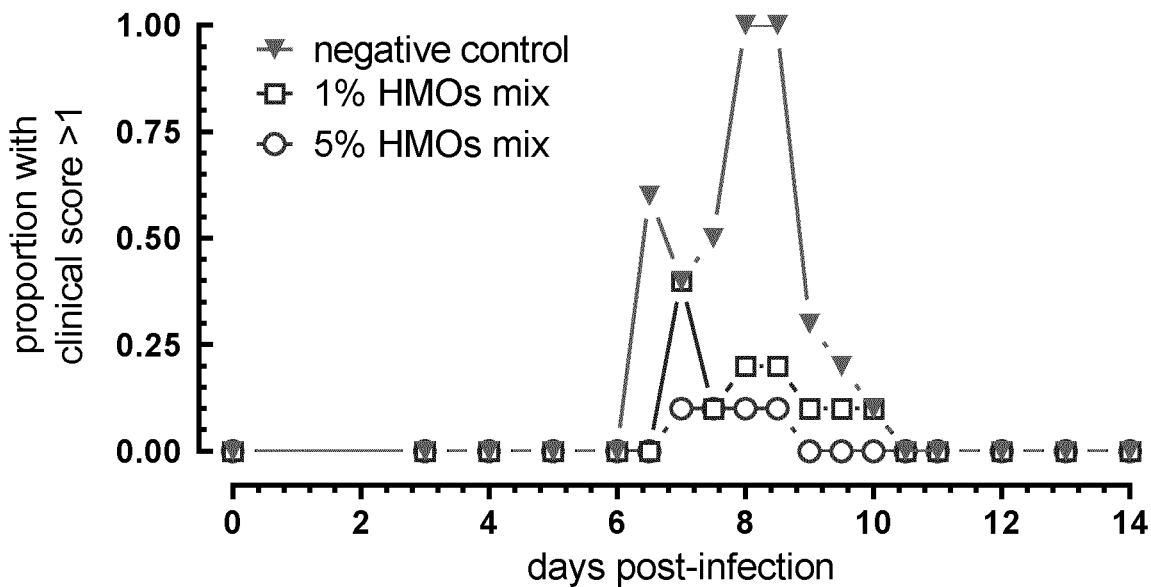

Ward et al., "In Vitro Fermentation of Breast Milk Oligosaccharides by Bifidobacterium Infantis and Lactobacillus Gasseri", Applied and Environmental Microbiology, vol. 72, Issue No. 06, Jun. 30, 2006, pp. 4497-4499.
Urashima et al. "Milk Oligosaccharides" Nova Biomedical Books, New York, 2011, pp. 695-724.
Edgar "Uparse: highly accurate OTU sequences from microbial amplicon reads" Nature Methods, Oct. 2013, vol. 10, No. 10, pp. 996-1000.
Klindworth et al. "Evaluation of general 16S ribosomal RNA gene PCR primers for classical and next-generation sequencing-based diversity studies" Nucleic Acids Research, 2013, vol. 41, No. 1, 11 pages.
Duska-Mcewen et al., "Human Milk Oligosaccharides Enhance Innate Immunity to Respiratory Syncytial Virus and Influenza in Vitro", Food and Nutrition Sciences, vol. 5, Issue No. 14, 2014, pp. 1387-1398.
Puccio et al., "Effects of Infant Formula With Human Milk Oligosaccharides on Growth and Morbidity: A Randomized Multicenter Trial", Journal of Pediatric Gastroenterology and Nutrition, vol. 64, Issue No. 4, 2017, pp. 624-631.
Preliminary Opinion for Appl No. 16809851.5 // 3389404 (1).
Preliminary Opinion for Appl No. 16809851.5 // 3389404 (2).
Preliminary Opinion for Appl No. 16809851.5 // 3389404 (3).

* cited by examiner

MIXTURE OF HUMAN MILK OLIGOSACCHARIDES(HMOS)

CROSS REFERENCE TO RELATED APPLICATIONS

The present application is a National Stage of International Application No. PCT/EP2016/081308, filed on Dec. 15, 2016, which claims priority to European Patent Application No. 15200067.5, filed on Dec. 15, 2015, and European Patent Application No. 16154144.6, filed on Feb. 3, 2016, the entire contents of which are being incorporated herein by reference.

FIELD OF THE INVENTION

The present invention relates to synthetic mixtures of Human Milk Oligosaccharides ("HMOs"), particularly of LNnT, LNT, 2'-FL, 3'-SL, 6'-SL and either DFL or 3-FL and applications of the mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al, Milk Oligosaccharides, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, several processes for synthesizing HMOs have been developed in recent years due to their roles in numerous human biological processes. In this regard, processes have been developed for producing HMOs by microbial fermentations, enzymatic processes, chemical syntheses, or combinations of these technologies. For example, by chemical processes, Galpβ1-4GlcNAcpβ1-3Galpβ1-4Glc or lacto-N-neotetraose ("LNnT") can be made as described in WO 2011/100980 and WO 2013/044928; Galpβ1-3GlcNAcpβ1-3Galpβ1-4Glc or lacto-N-tetraose ("LNT") can be synthesized as described in WO 2012/155916 and WO 2013/044928; 6'-O-sialyllactose ("6'-SL) can be synthesized as described in WO 2011/100979; a mixture of LNT and LNnT can be made as described in WO 2013/091660; 2'-O-fucosyllactose ("2'-FL") can be made as described in WO 2010/115934 and WO 2010/115935; 3-fucosyllactose ("3-FL") can be made as described in WO 2013/139344; and 6'-SL can be made as described in WO 2010/100979. As examples of biotechnological processes, WO 01/04341 and WO 2007/101862 describe how to make core human milk oligosaccharides optionally substituted by fucose or sialic acid, including LNnT, 6'-SL and 3'-O-sialyllactose ("3'-SL") using genetically modified *E. coli*; and WO 2015/032412 describes making 2'-FL and difucosyllactose or Fuc(α1-2)Gal(β1-4)[Fuc(α1-3)]Glc ("DFL") using genetically modified *E. coli*. As an example of enzymatic processes, sialylated oligosaccharides can be made as described in EP-A-577580.

Efforts have also been made to develop processes for synthesizing enzymatically mixtures of HMO oligosaccharides, without having to synthesize all of the component oligosaccharides of the mixture as described in WO 2012/156897 and WO 2012/156898. Such processes have provided reaction mixtures containing a plurality of different oligosaccharides.

Evidence is accumulating that the resident community of microbes, called the microbiota, in the human digestive tract plays a major role in health and disease. When the composition of the intestinal microbiota is thrown off balance, the human host can suffer consequences. Recent research has implicated intestinal microbiota imbalances in individual disorders as diverse as cancer, obesity, inflammatory bowel disease, psoriasis, asthma, and possibly even autism. Individual non-digestible fibres, including HMOs, are believed to positively modulate the microbiota, and they are of increasing interest for treating one or more of such disorders. However, many digestible fibres non-specifically modulate the microbiota while others are not able to provide sufficiently broad, but specific, modulation.

Therefore, there has been a need to specifically modulate the microbiota, so as to address individual disorders in different ways and also to address simultaneously multiple disorders. In particular, there has been a need for a composition that can be used for, inter alia, treating and/or preventing bacterial and viral infections, particularly in the intestinal and respiratory tracts, improving cognitive function and/or increasing the efficacy of anticancer agents against tumors.

SUMMARY OF THE INVENTION

A first aspect of this invention relates to a synthetic mixture of HMOs or a composition comprising thereof, said HMOs consisting essentially of LNnT, LNT, 2'-FL, 3'-SL, 6'-SL and either DFL or 3-FL, preferably DFL. This mixture can optionally include lactose. The mixture of HMOs preferably consists essentially of:
  i. about 55 wt % to about 75 wt % of 2'-FL, more preferably about 60 wt % to about 70 wt %;
  ii. about 2 wt % to about 10 wt % of LNnT, more preferably about 3 wt % to about 7 wt %;
  iii. about 10 wt % to about 20 wt % of LNT, more preferably about 12 wt % to about 18 wt %;
  iv. about 1 wt % to about 10 wt % of DFL or 3-FL, more preferably about 2 wt % to about 8 wt %;
  v. about 1 wt % to about 10 wt % of 3'-SL, more preferably about 2 wt % to about 8 wt %; and
  vi. about 5 wt % to about 15 wt % of 6'-SL, more preferably about 7 wt % to about 13 wt %.

A second aspect of this invention relates to a composition for use in: i) preventing and/or treating viral and/or bacterial infections in a human, particularly infants or young children; ii) specifically modulating the indigenous microbiota of a human, particularly infants or young children; and/or iii) improving the cognitive function of humans, particularly infants or young children. The composition comprises a synthetic mixture of HMOs of this invention consisting essentially of LNnT, LNT, 2'-FL, 3'-SL, 6'-SL and either DFL or 3-FL, preferably DFL, as described above. This composition contains a plurality of different HMOs with novel combinations of properties and biological activities. The composition is especially useful against viral and bacterial, intestinal infections through specific modulation of the intestinal microbiota by an increase in *Bifidobacterium*, modulation of intestinal binding of viruses and pathogenic bacteria to intestinal epithelial cells, and improvement of intestinal barrier function. The composition is also especially useful against viral and bacterial, respiratory tract infections by inhibiting pathogen binding to human epithelial cells.

In a particular embodiment, the composition of the present invention is for use in preventing and/or treating viral infections caused by Influenza virus.

A third aspect of this invention relates to a method of modulating the indigenous microbiota of a human to increase the abundance of Bifidobacterium, especially in order to increase the efficacy of anticancer agents against tumors in a human patient. The method involves administering to the human a synthetic mixture of HMOs of this invention consisting essentially of LNnT, LNT, 2'-FL, 3'-SL, 6'-SL and either DFL or 3-FL, preferably DFL, as described above. Bifidobacterium can act as an immune booster, hence the increase in its abundance can strengthen a cancer patient's response to an anticancer agent. This property makes the mixture suitable as an aid in cancer therapy.

A fourth aspect of this invention relates to a method of modulating the indigenous intestinal microbiota of a human to increase both Bifidobacterium and Barnesiella abundance and also to reduce the abundance of Ruminococcus gnavus. The method involves administering to the human a synthetic mixture of HMOs of this invention consisting essentially of LNnT, LNT, 2'-FL, 3'-SL, 6'-SL and either DFL or 3-FL, preferably DFL, as described above. The increased Bifidobacterium and Barnesiella abundance and reduced abundance of Ruminococcus gnavus render the human's intestinal milieu less prone to inflammation and provide improved intestinal barrier function. These effects can prevent and/or treat conditions such as inflammatory bowel disease, irritable bowel syndrome, and other conditions associated with inflammation and impaired gut barrier function.

A fifth aspect of this invention relates to a method of modulating the indigenous microbiota of a human to increase Bifidobacterium abundance and to at least maintain the abundance of Faecalibacterium. The method involves administering to the human a synthetic mixture of HMOs of this invention consisting essentially of LNnT, LNT, 2'-FL, 3'-SL, 6-'SL and either DFL or 3-FL, preferably DFL, as described above. Increasing the Bifidobacterium abundance and at least maintaining the abundance of Faecalibacterium render the human's intestinal milieu less prone to inflammation and provide improved intestinal barrier function. Preferably the abundance of Ruminococcus gnavus is reduced. These effects can prevent and/or treat conditions such as inflammatory bowel disease, irritable bowel syndrome, and other conditions associated with inflammation and impaired gut barrier function.

In both the fourth and fifth aspects of the invention, the abundance of Proteobacteria is also preferably reduced.

A sixth aspect of this invention relates to a method of preventing or treating viral and/or bacterial infections in a human, especially intestinal infections and infections of the respiratory tract. The method comprises administering, to the human, a synthetic mixture of HMOs of this invention consisting essentially of LNnT, LNT, 2'-FL, 3'-SL, 6'-SL and either DFL or 3-FL, preferably DFL, as described above.

A seventh aspect of this invention relates to a method of improving the cognitive function of humans, particularly infants. The method comprises administering, to the humans, a synthetic mixture of HMOs of this invention consisting essentially of LNnT, LNT, 2'-FL, 3'-SL, 6'-SL and either DFL or 3-FL, preferably DFL, as described above.

FIGURES

FIG. 1: Proportion of mice showing clinical score above 1, meaning they showed symptoms of sickness. (n=10 per group)

Figure 2:
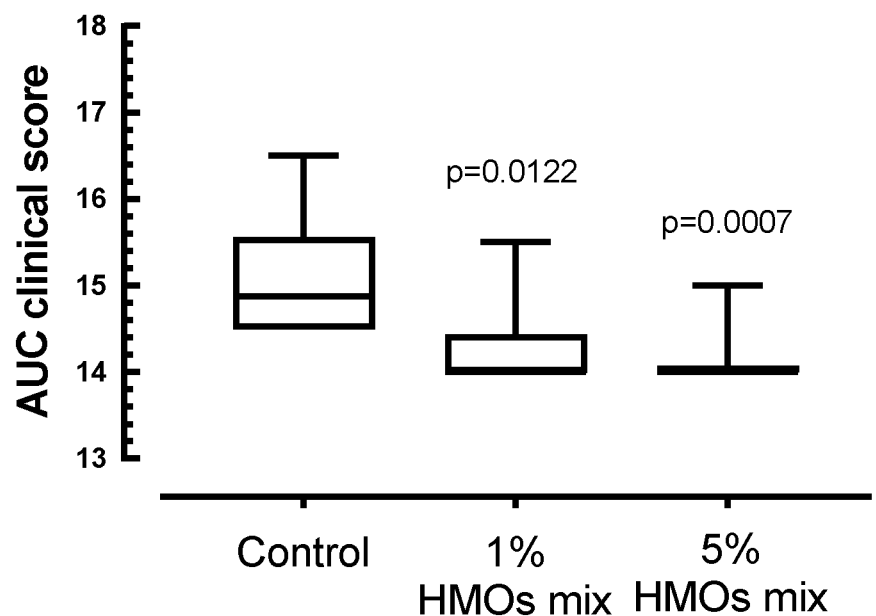

FIG. 2: Area under the curve (AUC) for clinical sickness score during the 14 days period after the influenza infection. (n=10 per group), statistical significance determined by Kruskal-Wallis (non-parametric) test with Dunn's multiple comparison test in comparison to control. The p-values are indicated.

Figure 3:
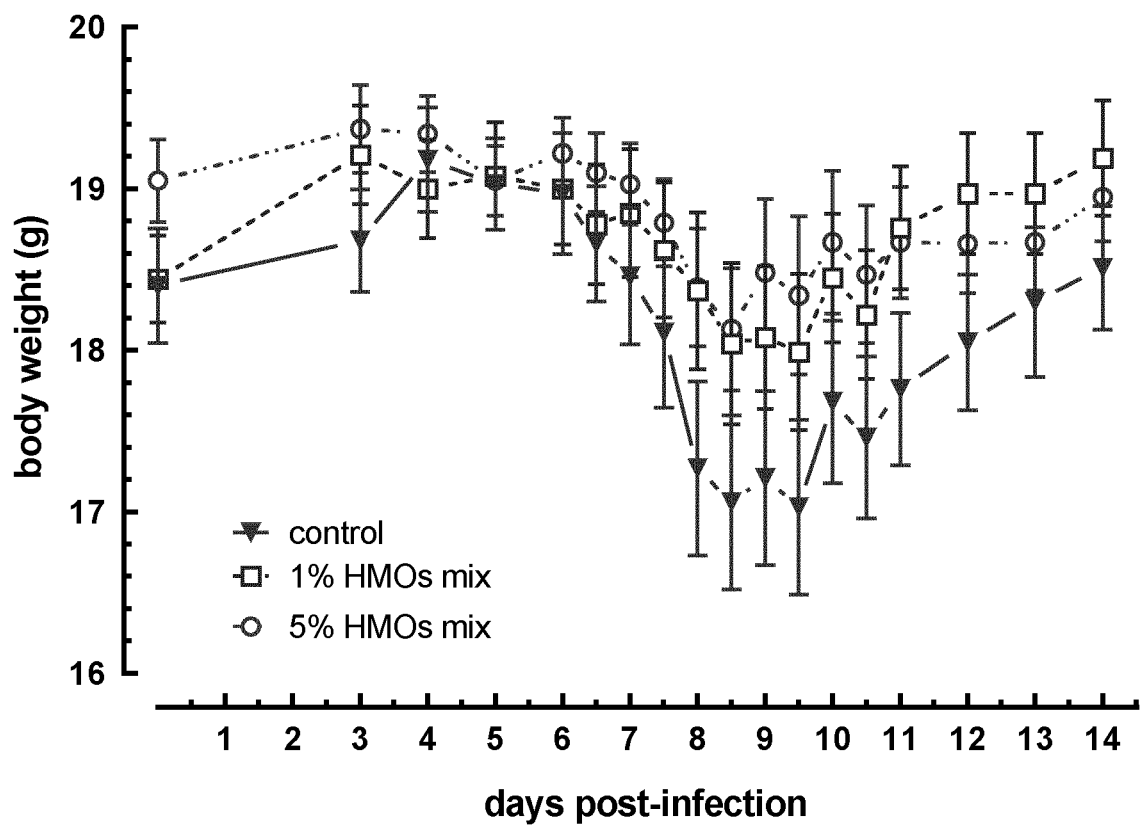

FIG. 3: Body weight (in grams) during the 14 days period after the influenza infection. The group receiving 1% or 5% HMOs mixture were losing significantly less body weight compared to the control group, indicating that these mice were less sick compared to control mice. (n=10 per group). Statistical test by 2-way ANOVA, body weight was significantly affected by time and treatment ($p<0.0001$) and control versus 1% HMOs mix had a $p=0.0002$, control versus 5% HMOs mix had a $p=0.0001$.

DETAILED DESCRIPTION OF THE INVENTION

As used herein, the following terms have the following meanings.

The term "infant" means a child under the age of 12 months.

The expression "young child" means a child aged between one and three years, also called toddler.

The expressions "a composition for infants or young children" and "a composition to be administered to infants or young children" can be used interchangeably.

In some embodiments, the composition comprising the HMOs mixture according to the invention is a nutritional composition. The expression "nutritional composition" means a composition which nourishes a subject. This nutritional composition is usually to be taken orally or intravenously, and it usually includes a lipid or fat source and a protein source. In a particular embodiment, the nutritional composition is a synthetic nutritional composition.

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

In accordance with this invention, it has been surprisingly discovered that a synthetic HMO mixture consisting essentially of LNnT, LNT, 2'-FL, 3'-SL, 6'-SL and either DFL or 3-FL, preferably DFL, and optionally lactose can provide an anti-infective composition for preventing or treating, bacterial or viral infections through specific modulation of the intestinal microbiota, binding of viruses, reduction in pathogenic translocation and improvement of intestinal barrier function. Further, the HMO mixture of this invention acts as a decoy receptor and binds to rotaviruses to prevent the rotaviruses from adhering to human intestinal cells. These properties, coupled with an improvement in intestinal barrier function, make the HMO mixture suitable for preventing and treating intestinal infections. In some aspects of the invention, the composition is therefore for use in preventing and/or treating viral and/or bacterial infections in a human, particularly infants or young children.

In a particular embodiment, the composition of the present invention is for use in preventing and/or treating viral infections caused by Influenza virus.

The composition of the present invention may be particularly used to prevent or treat the symptoms associated with the flu, such as fever, articular pain, headaches, tireness, body weight loss . . . .

The composition of the present invention may be particularly used to reduce medication use in case of flu. In a particular embodiment it may also prevent the use of antibiotics following a bacterial surinfection after the flu.

It has also been found that the HMO mixture of this invention can increase the brain ganglioside and glycoprotein sialic acid concentrations, leading to increased synaptogenesis and neurodevelopment. This makes the HMO mixture suitable for administration to humans, particularly infants, to improve their cognitive function.

The HMO mixture of this invention can also:
i) increase the indigenous intestinal abundance of *Bifidobacterium* and
ii) increase the intestinal abundance of *Barnesiella* and/or at least maintain the intestinal abundance of *Faecalibacterium*, and
iii) reduce the intestinal abundance of *Ruminococcus gnavus* and/or *Proteobacteria*.

These effects can render an intestinal milieu less prone to inflammation. Coupled with an improvement in intestinal barrier function, these effects of the HMO mixture can prevent and/or treat conditions such as inflammatory bowel disease, irritable bowel syndrome, and other conditions associated with inflammation and impaired barrier function.

Surprisingly, the increase of bifidobacteria in the gut, induced by the HMO mixture of this invention, increases the efficacy of anticancer agents against tumors. The bifidobacteria act as immune helpers, strengthening a cancer patient's response to an anticancer agent. This property makes the HMO mixture suitable as an aid in cancer therapy.

Preferably the HMO mixture of this invention contains: i) about 55 wt % to about 75 wt % of 2'-FL, more preferably about wt 60% to about wt 70%; ii) about 2 wt % to about 10 wt % of LNnT, more preferably about 3 wt % to about 7 wt %; iii) about 10 wt % to about 20 wt % of LNT, more preferably about 12 wt % to about 18 wt %; iv) about 1 wt % to about 10 wt % of DFL or 3-FL, more preferably about 2 wt % to about 8 wt %; v) about 1 wt % to about 10 wt % of 3'-SL, more preferably about 2 wt % to about 8 wt %; and vi) about 5 wt % to about 15 wt % of 6'-SL, more preferably about 7 wt % to about 13 wt %. The HMO mixture of this invention can also contain lactose, but it is not considered an active ingredient of the mixture.

The HMO mixture can be administered to a human in any suitable form such as, for example, a unit dosage form (for example, a tablet, a capsule, a sachet of powder, etc.) or a nutritional composition.

The unit dosage form can contain an acceptable carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the composition can be coated by standard aqueous or nonaqueous techniques.

A unit dosage form of this invention can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or nonaqueous liquid, containing a predetermined concentration of the mixture. An orally administered composition can include one or more binders, lubricants, inert diluents, flavouring agents, and humectants. An orally administered composition such as a tablet can optionally be coated and can be formulated so as to provide sustained, delayed or controlled release of the HMO mixture therein.

A unit dosage form of this invention can also be administered by rectal suppository, aerosol tube, naso-gastric tube or direct infusion into the GI tract or stomach.

A unit dosage form of this invention can also include therapeutic agents such as antiviral agents, antibiotics, probiotics, analgesics, and anti-inflammatory agents. The proper dosage of such a composition for a patient can be determined in a conventional manner, based upon factors such as the patient's immune status, body weight and age. In some cases, the dosage will be at a concentration similar to that found for the HMOs of the composition in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

The HMO mixture of this invention can also be added to a nutritional composition. For example, it can be added to an infant formula, a food composition, a rehydration solution, or a dietary maintenance or supplement for elderly individuals or immunocompromised individuals. The nutritional composition can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula. In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

Macronutrients such as edible fats, carbohydrates and proteins can also be included to such a nutritional composition. Edible fats include, for example, coconut oil, soy oil and monoglycerides and diglycerides. Carbohydrates include, for example, glucose, edible lactose and hydrolysed cornstarch. Proteins include, for example, soy protein, whey, and skim milk. Vitamins and minerals (e. g. calcium, phosphorus, potassium, sodium, chloride, magnesium, manganese, iron, copper, zinc, selenium, iodine, and Vitamins A, E, D, C, and B complex) can also be included in such a nutritional composition.

The nutritional composition may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The HMO mixture of the present invention may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The HMO mixture of the present invention may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

EXAMPLES

Example 1

A total of 50 healthy male and female subjects are recruited to participate in the study. After a screening visit and run-in period of 1-2 weeks, the subjects are selected and randomized into 2 groups, each of 25 subjects. One group is administered a treatment product containing 5 g of the following HMO mixture of this invention:
  i) 14.2 wt % of LNT
  ii) 5.3 wt % of LNnT
  iii) 63.7 wt % of 2'-FL
  iv) 4.2 wt % of DFL,
  v) 3.7 wt % of 3'-SL and
  vi) 8.9 wt % of 6'-SL The other group is administered a placebo (containing 2 grams of glucose). The treatment product and the placebo are in powder form in a unit dosage container.

The subjects are eligible to participate if they are at least 18 years of age. All recruited subjects are able and willing to understand and comply with the study procedures. Subjects are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Subjects are familiarised with an interactive internet enabled system which records data daily and are provided with either treatment or control products. Subjects are reminded not to change their usual diet during the study. Blood samples are collected for biomarker studies. The faecal samples are stored at −80° C. until analysis. Faecal samples are subjected to 16S rRNA sequencing analysis.

The study runs for 8 weeks with the subjects consuming either a placebo or a treatment product daily. Subjects are instructed to consume the products in the morning with breakfast. Compliance is monitored through the interactive internet enabled system. The subjects also use the system to record:
  Bristol Stool Form (BSF) scale information,
  symptom information such as abdominal pain, abdominal discomfort, abdominal cramping, abdominal bloating, and abdominal fullness,
  additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each subject has an exit visit with the medical team. Faecal samples and blood samples are collected and analysed as before.

The faecal analysis indicates that the subjects treated with the HMO mixture of this invention have increased abundance of *Bifidobacterium* and *Barnesiella* and reduced abundance of *Firmicutes*, especially *Clostridia*, and *Ruminococcus gnavus*. The abundance of *Faecalibacterium* is unchanged in these subjects. The abundance of *Proteobacteria* is decreased in these subjects.

Example 2

Twenty 7-week-old C57BL/6J female mice are individually housed to avoid contamination between mice and provided with irradiated food and water. The mice are separated into 2 groups, each of 10 mice.

The mice are treated with ampicillin (0.5 g/liter) in their drinking water, which is changed every 3 days. After 1 week, the ampicillin addition to the drinking water is terminated. Thereafter, 1 group is administered a treatment product containing the following HMO mixture of this invention:
- 14.2 wt. % of LNT
- 5.3 wt. % of LNnT
- 63.7 wt. % of 2'-FL
- 4.2 wt. % of DFL,
- 3.7 wt. % of 3'-SL and
- 8.9 wt. % of 6'-SL.

The treatment product is added to the drinking water of 1 group at a total concentration of 40 mg/ml. The other group receives drinking water with 40 mg/ml of glucose. Fresh water is administered daily, and all mice have free access to the drinking water. The mice are fed a rodent chow and are given fresh chow daily.

Two days after termination of the ampicillin treatment, mice of each group is infected by oral gavage with a vancomycin-resistant *Enterococcus faecium* strain (VRE). Fresh faecal pellets are collected at different time points to determine the VRE levels. VRE is quantified by plating serial dilutions of faecal pellets on Enterococcosel agar plates with vancomycin. VRE colonies are identified by appearance and confirmed by Gram staining. PCR of the vanA gene, which confers resistance to vancomycin, is used to confirm the presence of VRE in infected mice.

The mice are monitored for 2 weeks and are then euthanized. Luminal contents from the ilium, cecum and colon are collected and immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, e1 (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the mice treated with the HMO mixture of this invention, VRE colonisation is reduced to undetectable levels within 14 days. The density of VRE reduces within 5 days. The mice treated with the HMO mixture also showed a higher abundance of *Porphyromonadaceae*, especially *Barnesiella*. The untreated mice continue to harbour large numbers of VRE throughout the intestine.

Example 3

An example of the composition of a nutritional composition (e.g. an infant formula) comprising the HMOs blend of the present invention is given in the below table 1. This composition is given by way of illustration only.

TABLE 1 an example of the composition of a nutritional composition (e.g. an infant formula)

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 10.6 | 70.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides (HMOs) | 2FL (g) | 0.39 | 2.56 |
| | LNnT (g) | 0.03 | 0.2 |
| | LNT (g) | 0.08 | 0.56 |
| | DFL (g) | 0.03 | 0.2 |
| | 3SL (g) | 0.03 | 0.2 |
| | 6SL (g) | 0.05 | 0.36 |

Example 4

Another example of the composition of a nutritional composition (e.g. an infant formula) comprising the HMOs blend of the present invention is given in the below table 1. This composition is given by way of illustration only.

TABLE 2 an example of the composition of a nutritional composition (e.g. an infant formula)

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |

TABLE 2-continued an example of the composition of a nutritional composition (e.g. an infant formula)

| Nutrients | | per 100 kcal | per litre |
|---|---|---|---|
| α-Linolenic acid (mg) | | 101 | 675 |
| Lactose (g) | | 10.9 | 72.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides (HMOs) | 2FL (g) | 0.19 | 1.28 |
| | LNnT (g) | 0.015 | 0.1 |
| | LNT (g) | 0.042 | 0.28 |
| | DFL (g) | 0.015 | 0.1 |
| | 3SL (g) | 0.015 | 0.1 |
| | 6SL (g) | 0.027 | 0.18 |

Example 5

Mouse Influenza Virus Infection Model.

Mice (5 weeks old; n=30) were randomly allocated to one of the following groups. A, control (n=10); B, 1% mixture of HMOs (n=10); C, 5% mixture of HMOs (n=10). See below table 3 for the composition of the HMOs blend. The HMOs were provided in drinking water. All animals had free access to same diet (KLIBA 2122). After 2 weeks mice were challenged with Influenza strain PR8 at a dose of 100 PFU per mouse by intranasal inoculation. Mice were monitored for the next 14 days to assess clinical score of illness symptoms and body weight loss.

The results (see FIGS. 1, 2 and 3) show that the HMOs mixture as claimed herein shows protection of sickness symptoms and body weight loss caused by the influenza virus infection.

TABLE 3

Composition of HMOs mixture used in this experiment.

| | g/100 mL | |
|---|---|---|
| | 1% | 5% |
| 2'FL (g) | 0.64 | 3.2 |
| LNnT (g) | 0.05 | 0.25 |
| LNT (g) | 0.14 | 0.7 |
| 3'SL (g) | 0.05 | 0.25 |
| 6'SL (g) | 0.09 | 0.45 |
| diFL (g) | 0.05 | 0.25 |

The invention claimed is:

1. A method to prevent and/or treat symptoms associated with infection by Influenza virus and/or to reduce medication use in case of infection by Influenza virus, in an infant or a young child, the method comprising:
   administering to the infant or young child a composition comprising a mixture of human milk oligosaccharides (HMOs) consisting essentially of
   about 2 wt % to about 10 wt % of lacto-N-neotetraose (LNnT),
   about 10 wt % to about 20 wt % of lacto-N-tetraose (LNT),
   about 55 wt % to about 75 wt % of 2'-O-fucosyllactose (2'-FL),
   about 1 wt % to about 10 wt % of 3'-O-sialyllactose (3'-SL),
   about 5 wt % to about 15 wt % of 6'-O-sialyllactose (6'-SL) and
   about 1 wt % to about 10 wt % of difucosyllactose (DFL).

2. The method according to claim 1, wherein the mixture of HMOs is administered in an amount effective to modulate intestinal microbiota of the infant or young child.

3. The method according to claim 1, wherein the mixture of HMOs is administered in an amount effective to improve cognitive function of the infant or young child.

4. The method according to claim 1, wherein the mixture of HMOs consists of the LNnT, the LNT, the 2'-FL, the 3'-SL, the 6'-SL and the DFL.

5. The method according to claim 1, wherein the abundance of *Bifidobacterium* or of both *Bifidobacterium* and *Barnesiella* in intestinal microbiota of the infant or young child is increased by the administering of the mixture of HMOs.

6. The method according to claim 5, wherein the abundance of *Ruminococcus gnavus* is decreased and/or the abundance of *Proteobacteria* is decreased and/or the abundance of *Faecalibacterium* is maintained in intestinal microbiota of the infant or young child by the administering of the mixture of HMOs.

7. The method according to claim 1, wherein the mixture of HMOs consists essentially of:
   i. about 60 wt % to about 70 wt % of 2'-FL;
   ii. about 3 wt % to about 7 wt % of LNnT;
   iii. about 12 wt % to about 18 wt % of LNT;
   iv. about 2 wt % to about 8 wt % of DFL;
   v. about 2 wt % to about 8 wt % of 3'-SL; and
   vi. about 7 wt % to about 13 wt % of 6'-SL.

\* \* \* \* \*